United States Patent
Wittkampf

[19]

[11] Patent Number: 5,983,126
[45] Date of Patent: *Nov. 9, 1999

[54] CATHETER LOCATION SYSTEM AND METHOD

[75] Inventor: Frederik H. M. Wittkampf, Bilthoven, Netherlands

[73] Assignee: Medtronic, Inc., Minneapolis, Minn.

[*] Notice: This patent is subject to a terminal disclaimer.

[21] Appl. No.: 08/904,588

[22] Filed: Aug. 1, 1997

Related U.S. Application Data

[63] Continuation of application No. 08/561,773, Nov. 22, 1995, Pat. No. 5,697,377.
[51] Int. Cl.$^6$ .................. A61B 5/04; A61N 1/32
[52] U.S. Cl. .................. 600/509; 128/898; 607/101; 607/122
[58] Field of Search .................. 600/407, 424, 600/508, 509, 515; 128/899; 607/101, 122, 154

[56] References Cited

U.S. PATENT DOCUMENTS

| | | | |
|---|---|---|---|
| 4,304,239 | 12/1981 | Perlin | 128/642 |
| 4,317,078 | 2/1982 | Weed et al. | 324/208 |
| 4,522,212 | 6/1985 | Gelinas et al. | 128/642 |
| 4,649,924 | 3/1987 | Taccardi | 128/642 |
| 4,660,571 | 4/1987 | Hess et al. | 128/784 |
| 4,699,147 | 10/1987 | Chilson et al. | 128/642 |
| 5,042,486 | 8/1991 | Pfeiler et al. | 128/653 R |
| 5,099,845 | 3/1992 | Besz et al. | 128/899 X |
| 5,158,092 | 10/1992 | Glace | 128/705 |
| 5,297,549 | 3/1994 | Beatty et al. | 128/642 |
| 5,311,866 | 5/1994 | Kagan et al. | 128/642 |
| 5,375,596 | 12/1994 | Twiss et al. | 128/653.1 |
| 5,377,678 | 1/1995 | Dumoulin et al. | 128/653.1 |
| 5,383,454 | 1/1995 | Bucholz | 128/653.1 |
| 5,391,199 | 2/1995 | Ben-Haim | 607/122 |
| 5,397,339 | 3/1995 | Desai | 607/116 |
| 5,398,691 | 3/1995 | Martin et al. | 128/653.1 |
| 5,429,132 | 7/1995 | Guy et al. | 128/899 X |
| 5,443,066 | 8/1995 | Dumoulin et al. | 128/653.1 |
| 5,443,489 | 8/1995 | Ben-Haim | 607/115 |
| 5,480,422 | 1/1996 | Ben-Haim | 607/122 |
| 5,546,951 | 8/1996 | Ben-Haim | 128/702 |
| 5,558,091 | 9/1996 | Acker et al. | 128/653.1 |
| 5,568,809 | 10/1996 | Ben-Haim | 128/656 |

FOREIGN PATENT DOCUMENTS

WO 92/03090  3/1992  WIPO.

*Primary Examiner*—Jeffrey R. Jastrzab
*Attorney, Agent, or Firm*—Michael J. Jaro; Harold Patton

[57] ABSTRACT

A system and method are provided for catheter location mapping, and related procedures. Three substantially orthogonal alternating signals are applied through the patient, directed substantially toward the area of interest to be mapped, such as patient's heart. The currents are preferably constant current pulses, of a frequency and magnitude to avoid disruption with ECG recordings. A catheter is equipped with at least a measuring electrode, which for cardiac procedures is positioned at various locations either against the patient's heart wall, or within a coronary vein or artery. A voltage is sensed between the catheter tip and a reference electrode, preferably a surface electrode on the patient, which voltage signal has components corresponding to the three orthogonal applied current signals. Three processing channels are used to separate out the three components as x, y and z signals, from which calculations are made for determination of the three-dimensional location of the catheter tip within the body. An easy calibration procedure, which can be performed separately or during the mapping, is used to calibrate the system and provide the correlations between respective x, y and z sense signals and dimensional locations. The procedure is particularly applicable for catheter mapping prior to ablation, and for repositioning the catheter tip at precise locations for the desired ablations. The procedure is also applicable for other techniques where position must be remembered and re-found with accuracy, such as in mapping coronary stenosis and/or placing stents. Although the invention provides the greatest benefit in 3-dimensional applications, it is also useful for one and two dimensional applications.

34 Claims, 6 Drawing Sheets

CATHETER LOCATION SYSTEM AND METHOD

This is a CONTINUATION of application Ser. No. 08/561,773 filed on Nov. 22. 1995 now U.S. Pat. No. 5,697,377.

BACKGROUND OF THE INVENTION

This invention relates to systems and methods for mapping catheter electrode position within a patient's body and, more particularly, a system and method which enables automatic real time three-dimensional measurement of catheter electrode position with an accuracy well less than 1 cm.

As is known, accurate position information is necessary for mapping, or localizing an accessory atrioventricular pathway. In this case, one can localize the ventricular or atrial insertion site of the pathway during antegrade or retrograde conduction through the pathway. The need for accurate positioning information is further illustrated by the standard method of cardiac mapping and subsequent ablation of the site of a ventricular tachycardia in a patient. The catheter is introduced into the atrium or ventricle, and the tip is positioned at an endocardial site. A tachycardia is induced, and the tip is moved to different positions, where the timing of sensed intracardiac signals is compared with ECG signals. Each position and the local activation moment must be accurately determined and recorded, so that an accurate map can be made from which the tachycardia focus can be determined. Following the mapping, the ablation tip must be accurately re-positioned with respect to the focus. This re-positioning places a great importance on being able to obtain accurate tip position information when and as the tip is moved to a position. Further, it is well known that frequently multiple ablations are often necessary in a relatively small area within the heart, in order to eliminate arrhythmogenic foci. Accordingly, the catheter is sequentially positioned at slightly different positions close to the focus, for producing lesions in the heart wall. These lesions are produced at different locations in order to ensure elimination of the foci. At present, it is difficult to obtain accurate and reliable information concerning the distances between successive ablation sites.

During hemodynamic and electrophysiologic cardiac catheterization procedures, cardiologists generally employ a monoplane and sometimes biplane fluoroscopic imaging to estimate the position of the catheter within the heart. However, with fluoroscopy, it is not yet possible to obtain automatic and objective three-dimensional information about the catheter position without laborious three-dimensional reconstruction from fluoroscopic images. As is readily understood, automatic measurement of the catheter position would be extremely useful during many interventional catheterization procedures.

Systems for obtaining three-dimensional catheter position data are known, but have serious limitations. For example, a magnetic system employs a special element in the catheter tip, the size and configuration of which make it useful for only certain catheter types. Given the many different types of catheters in use for different applications, a system and technique that would be able to accurately locate the position of any type catheter would constitute a significant advance.

The patent art contains a great many devices and systems directed toward catheter location. These systems embrace a number of different approaches, such as securing an inductor coil adjacent to the catheter tip with leads extending from the coil along the catheter for connection to external indicating equipment; positioning a varying magnetic field responsive component on the catheter or implement to be positioned, and using a movable external magnetic field source; use of a probe which generates a small magnetic field which is disturbed by a magnetically permeable metal in the device to be positioned; and the construction of various types of cardiac mapping probes and electrode configurations. However, these approaches have not proven commercially successful for one reason or another, and there remains a substantial need in the art for an improved technique of catheter mapping, particularly as applicable to cardiac catheterization and ablation procedures.

SUMMARY OF THE INVENTION

In accordance with the above need in the art, there is provided a catheter mapping system and method for mapping locations within a patient, which provides an improved accuracy of location, the accuracy being on the order of a few mm. The invention involves applying three orthogonal (x, y, z) current signals through the patient, directed substantially toward the area to be explored, such as the patient's heart, each of the signals having a respective characteristic which renders it distinguishable from the other two orthogonal signals. The catheter, which has been introduced into the body area to be explored, has a tip electrode or another mapping electrode positioned in the vicinity of the distal tip, which is connected through to three sensing channels. The sensing channels sense the signals induced at the electrode location by the three respective applied signals, which sensed signals are used to calculate the location of the electrode. A simple calibration procedure uses two electrodes at a known interelectrode distance on the catheter, and three quick measurements for determining the correlation of the respective sensed x, y and z signals with the tip position.

In the preferred embodiment, the external signals are orthogonal, but can be slightly off orthogonal. The externally applied signals are suitably constant current pulse currents at frequencies in the range of about 25–50 kHz, with the constant current pulses having a current in a range centered around about 0.1 mA. While these parameters have been found to be useful for avoiding interference with ECG pickups, other parameters can be used. The sensed x, y and z signals are separated by digital filters, or other suitable narrow pass filters, with the resulting signals passed through a low pass filter which has a cutoff designed to eliminate variations due to cardiac contraction and patient respiration.

The ready availability of accurate three dimensional position data will allow for numerous improvements in visualization of catheter position. While the X-ray state of the art only presents two separate images in two usually perpendicular directions, three dimensional information allows for a three dimensional presentation of catheter tip position to cardiologists. This will make catheterization a lot easier and quicker, and meet a substantial long-existing need.

DESCRIPTION OF THE PREFERRED EMBODIMENT

Figure 1:
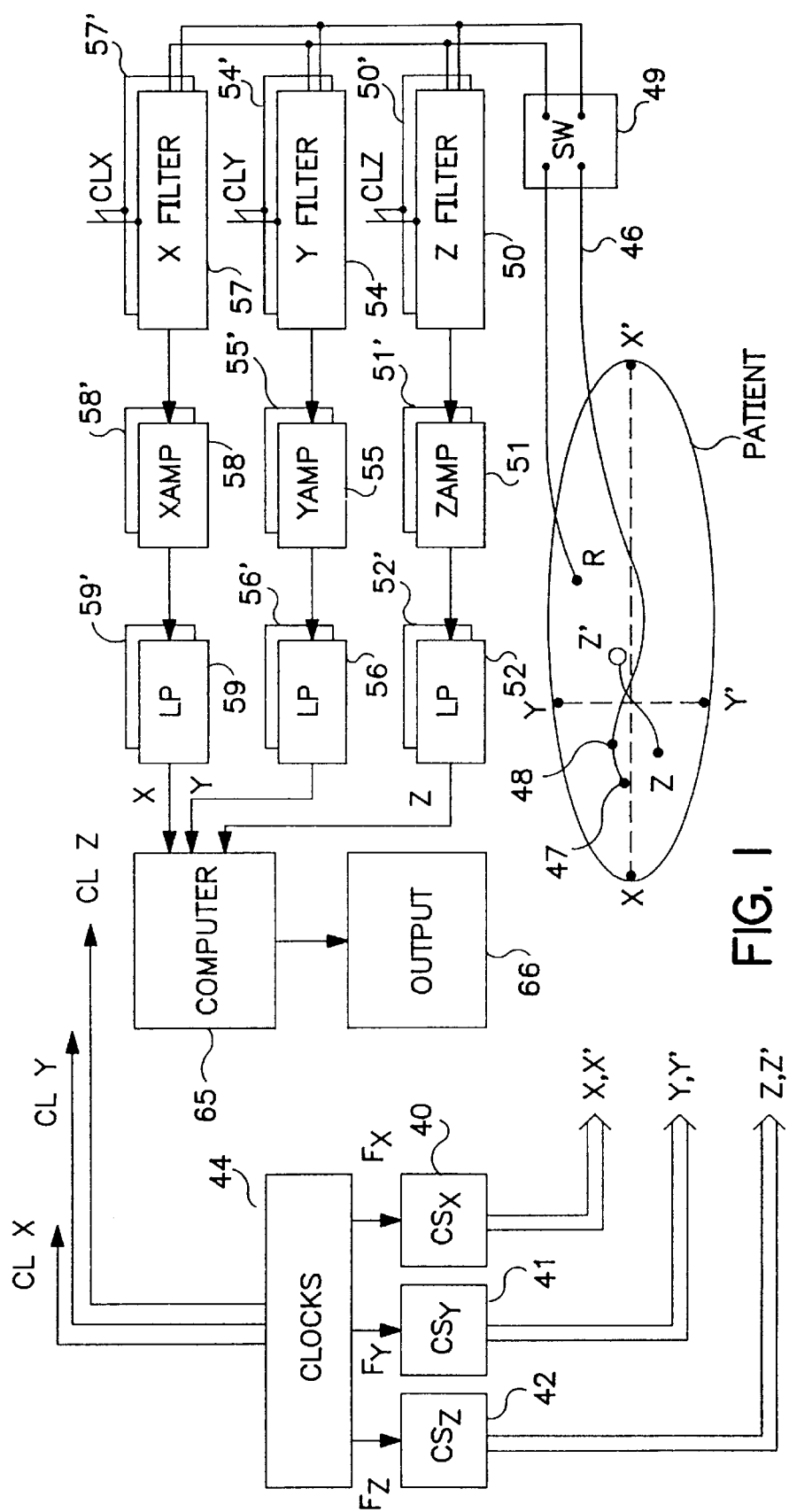
FIG. 1 is a block diagram illustrating the major components of the system of this invention as used for catheter mapping and related procedures.

This invention is based upon using the patient, and in a specific embodiment example, the patient's heart, as a potentiometer in three orthogonal directions. Orthogonal high-frequency current sources are utilized to transmit a relatively low current in each of three respective orthogonal directions through the patient, directed toward or near the body area of interest. As seen in FIG. 1, respective current sources 40, 41 and 42 are used to generate signals applied to electrodes which are shown diagrammatically as electrode pairs x, x'; y, y'; and z, z'. A catheter 46 is introduced into the patient, and for purposes of the ongoing discussion it will be assumed that the distal end of the catheter is introduced into the patient's heart. The catheter has at least two electrodes, illustrated at 47, 48. Electrode 47 is at about the tip end of the catheter, and can be positioned at or adjacent to the heart wall area of interest. As used herein, the tip electrode may be actually at the tip, or displaced somewhat proximally from the tip but in the distal tip region of the catheter. The second electrode 48 is positioned a predetermined distance D from the electrode 47. Although just two such electrodes are shown, the catheter may contain three, four or more electrodes, so long as it contains at least a position-detecting electrode, preferably at or near the tip, and provides a pair of electrodes separated by a predetermined distance D, for calibration purposes as set forth below. Note that a PTCA catheter can have two electrodes near its tip, or on opposite sides of the balloon, with suitable connections for use in the practice. of this invention.

Figure 2A:
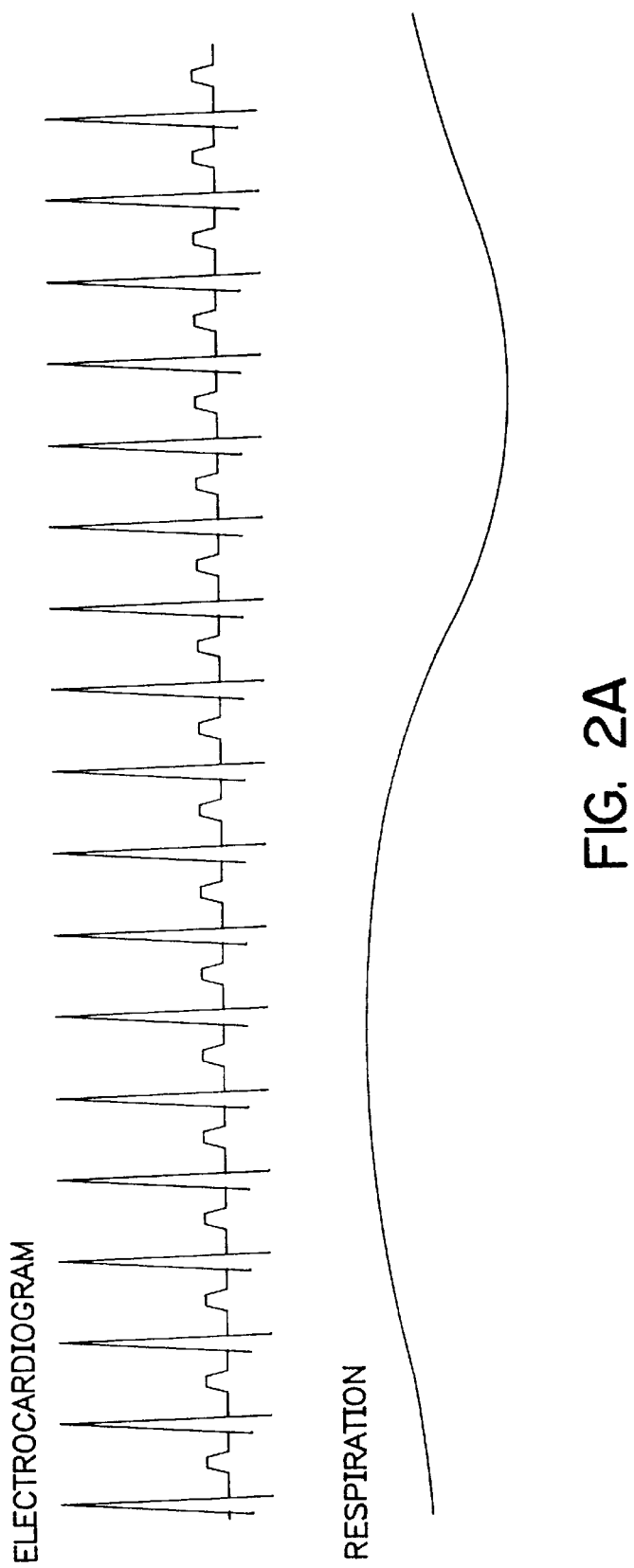
FIG. 2(a) shows a normal electrocardiogram above and a signal representative of respiration below, illustrating the relative frequencies.

In a first embodiment, the three electrical signals applied to the patient are high-frequency constant current pulse signals, of the form illustrated in FIG. 2A, each at a slightly different frequency. For example, the current source which drives the x, x' electrodes, designated $CS_x$, may operate at 30 kHz, with a current of about 0.1 mA; $CS_y$ operates at 31 kHz; and $CS_Z$ operates at 32 kHz. In the alternative, all three sources can operate at about the same frequency, but are time multiplexed so that they can be distinguished upon subsequent pick-up of sensed signals. The important distinction is that some characteristic such as frequency, phase or time is adjusted for each of the three applied signals, so that three signals can be sensed in the patient and then separated out as respective x, y and z signals.

It is to be noted that the range of 25–50 kHz is advantageous for practice of this invention, because it is well above the usual upper cut off frequency of bandpass endocardial electrogram amplifiers. Lower frequencies may also be used, but in such case specially trimmed filters are required for all electrogram amplifiers to eliminate the external signals. If, however, the invention is practiced with procedures where no endocardial electrograms are recorded, e.g. PTCA, then the external source frequencies may be much lower. Likewise, the orthogonal signals may have any current level suitable for avoiding noise pickup in other signals. And while current pulses are preferred because they eliminate the influence of varying skin contact impedance, the signals may be voltage pulses in some applications. Thus, the optimum frequency, as well as the signal level, will depend upon the application.

Continuing with the illustration of the invention, and assuming three different frequency external signals, the mathematical basis for determining a position of the catheter tip is now explained. Still referring to FIG. 1, in the method of intracardiac mapping of this invention, the tip or mapping electrode 47 is connected through to the three detection filters 50, 54, 57, each of which is adjusted to be sensitive to a respective one of the three current source frequencies. At any given location, for each orthogonal current a voltage is sensed between electrode 47 and reference electrode R, suitably a surface electrode on the patient's skin. Presuming that the body behaves linearly, the three different measured voltages give unique x,y and z values for the location of the tip electrode 47 within the patient's body, as follows:

$V_x = ax$ $V_y = by$ $V_z = cz$

The constants, or sensitivities, a, b and c, are unknowns which must be determined, and are expressed in mV/mm. In order to automatically calibrate, i.e., determine the three constants, in the preferred embodiment of this invention a catheter is employed that has two electrodes with a known interelectrode distance (D, in mm). One of the two electrodes may be the tip electrode, or the two electrodes may be two separate electrodes, such as two electrodes of a quadripolar catheter. This calibration arrangement requires two sets of equally sensitive detection amplifiers and signal processing paths for each direction as indicated diagrammatically in FIG. 1. Since each of the two electrodes picks up a voltage for each of the x, y and z currents, the following equations are applicable:

$V_{x1} = ax_1$, $V_{y1} = by_1$, and $V_{z1} = cz_1$ $V_{x2} = ax_2$, $V_{y2} = by_2$, and $V_{z2} = cz_2$ To calculate the unknowns a, b and c, it is necessary to use the measured value $\Delta V_x = V_{x2} - V_{x1}$ along with the unknown $\Delta x = x_2 - x_1$; $\Delta V_y = V_{y2} - V_{y1}$ together with $\Delta y = y_2 - y_1$ and $\Delta V_z = V_{z2} - V_{z1}$ together with $\Delta z = z_2 - z_1$. Then, knowing that $\Delta V_x = a\Delta x$, $\Delta V_y = b\Delta y$, and $\Delta V_z = c\Delta z$, and $\Delta X^2 + \Delta y^2 + \Delta z^2 = D^2$, one obtains:

$$\left(\frac{\Delta V_x}{a}\right)^2 + \left(\frac{\Delta V_y}{b}\right)^2 + \left(\frac{\Delta V_z}{c}\right)^2 = D^2$$

With $\Delta V_x$, $\Delta V_y$, and $\Delta V_z$ as measured, and D a known, $a^2$, $b^2$, and $c^2$ can be calculated. To simplify, let $1/a^2 = A$, $1/b^2 = B$, and $1/c^2 = C$, and $\Delta V_x^2 = X$, $\Delta V_y^2 = Y$ and $\Delta V_z^2$. This produces the following simplified equation:

$AX + BY + CZ + D^2$, where X, Y and Z are measured and D is the known interelectrode distance. It is now required only to obtain measurements for three such equations, by placing the catheter in three different orientations, in the same heart chamber or other body area. This does not require any extra procedure, because the catheter in any event is being continuously manipulated within the heart during catheterization. Note that it is not necessary to obtain these three orientations separately at the beginning of the procedure. Indeed, earlier position data can be corrected with later obtained calibrations. When the three sets of orientation data are obtained, the three simultaneous equations can be solved for A, B and C, the calibration values of a, b and c can then be calculated. While theoretically there are always two solutions for a, b and c from A, B and C, only the positive solution is the correct one.

In practice, the system may not be ideally homogeneous, meaning that any given set of obtained measurements is not absolutely correct. This is not a basic problem to obtaining accurate measurements, since the calculations can be continuously performed automatically during catheterization, and the results can be averaged. Thus, as long as the catheter is being manipulated, the calibration measurements and calculations can be repeated any number of times, and a resulting average obtained that provides a very real and accurate position determination. Note also that it is easy with this invention to calculate the calibration constants, or sensitivities, for different areas of the heart chamber. This could be useful since the measurements may not be precisely linear. By recalculating the calibration constants for different areas of the heart chamber, calculated relative positions can be reliably obtained for clinical use in mapping and ablation purposes.

Even without any calibration, a catheterization can be performed by assuming a "ballpark" sensitivity based, for example, on the weight or thorax dimensions of the patient. Note also that it is not usually necessary to map the whole heart chamber. Mapping and subsequent ablation is usually only performed in a certain part or area of the chamber where the arrhythmia originates. Linearity is much better when the mapping is confined to a limited area of that heart chamber.

In another embodiment of the invention, calibration can be achieved without using two electrodes in the heart, by assuming certain cardiac dimensions while only measuring $V_x$, $V_y$, and $V_z$ on the mapping electrode. For example, before entering the left ventricle, the catheter has to be manipulated through the aorta descendens, the aortic arc, and the aortic valve. With the patient on his or her back, the depth from the aorta descendens to the aortic valve is approximately 5 cm. The distance from the aortic valve to the left ventricular apex is known to be close to 10 cm. Using such approximate distance figures, together with the measured voltages at those sites, it is possible to generate a sensitivity calibration when the system is "told" where, in an anatomical sense, the catheter electrodes are positioned. This results in catheter positions inside a normalized left ventricle. The same technique can be used in other heart chambers for obtaining reliable position data.

Referring again to FIG. 1, catheter 46 is shown having a tip electrode 47, which is manipulated into some position within the heart chamber. A reference electrode R, on the surface of the patient's body, is connected to a lead to provide a reference potential. For making position measurements, the sensed voltage between tip electrode 47 and electrode R is connected through a switch matrix 49 to each of the three filters 50, 54 and 57, which are digital filters or other suitable narrow bandpass filters designed to pick up the respective signals generated at 40, 41 and 42 respectively. The three current sources are driven by respective clocks indicated at 44, which generate the basic timing signals at $f_x$, $f_y$ and $f_z$. These clock signals drive the current source generators, and also are connected to the respective x, y and z filters, for time sampling of the received signals as illustrated in FIG. 2(a) at points $V_1$ and $V_2$. The output of each of the filters 50, 54 and 57 is coupled through a corresponding amplifier 51, 55, 58, and then through a low pass filter 52, 56, 59. The low pass filters have a cutoff of about 0.1 Hz, to filter out any more quickly moving variations in the signal from each amplifier. The purpose of this is to avoid problems arising from heart contraction and patient respiration. Accordingly, the low pass filters suitably have a long time constant in the range of 5–10 seconds, so as to filter out the cardiac and respiratory movements. However, it is to be noted that in some applications the respiration and cardiac movement information may be useful, such that use of the low pass filters is an option.

Figure 2B:
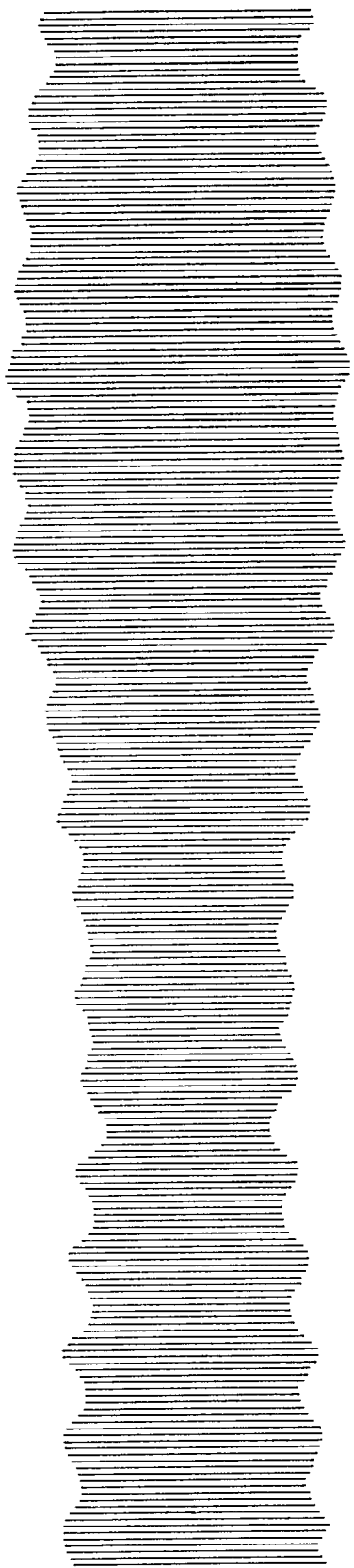
FIG. 2(b) illustrates a sensed location signal, and shows variations due to cardiac contraction and patient respiration.
Figure 2C:
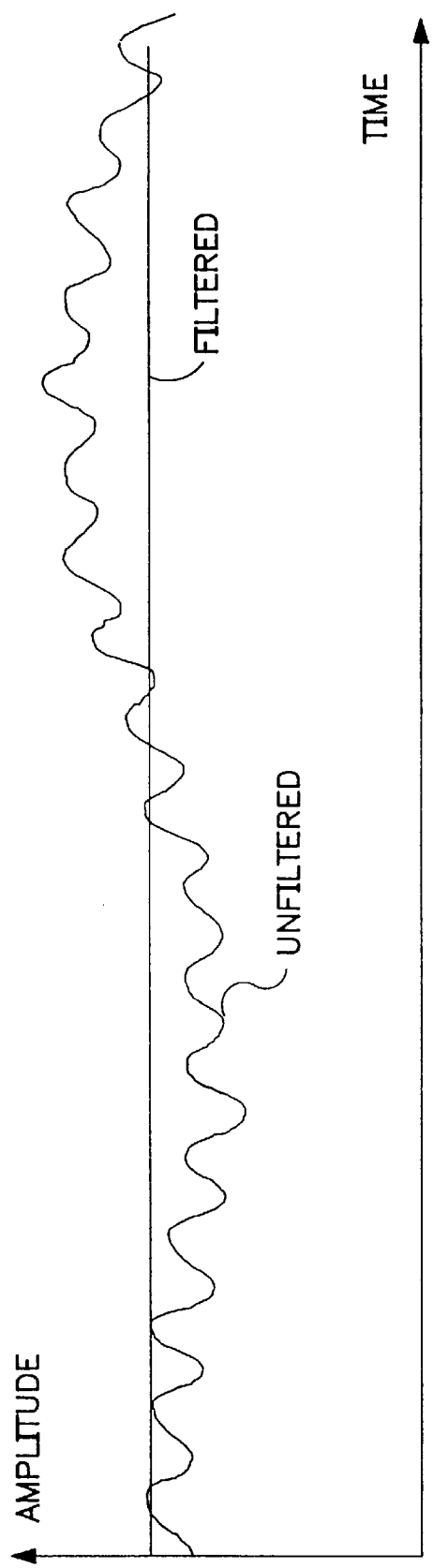
FIG. 2(c) illustrates the sensed location signal-with the high frequency filtered out, but still containing variations due to contraction and respiration (Vc), and the signal after the low frequencies have also been filtered out (V).

FIGS. 2(a), 2(b) and 2(c) illustrate the effect of contraction and respiration on the sensed x, y and z signals, and how these effects can be filtered out. FIG. 2(a) shows an electrocardiogram and a respiration signal; FIG. 2(b) shows the sensed signal which has been sampled at the plus and minus peaks, to develop a signal corresponding to the difference between the plus and minus portions of the sensed 30 kHz pulses. The amplitude of the sensed signal is illustrated as varying due to respiration and contraction, giving rise to a signal $V_c$, as illustrated in FIG. 2(c). Such signal changes are removed by the low pass filter, resulting in an accurate position signal of voltage V, illustrated in FIG. 2(c).

The x, y and z outputs from the three channels shown in FIG. 1 are connected to a computer 65, or equivalent apparatus, for calculation of each three-dimensional location. The outputs are connected to a suitable output, or display 66, for vertical real time display. As discussed further below, position data- can be stored for re-display later.

Referring back to FIG. 1, during the calibration steps each of the electrodes of the electrode pair on catheter 46 that is used for calibration is connected to a pair of z processing channels, a pair of y processing channels, and a pair of x processing channels. Thus, the two signals are inputted to z filters 50, 50'; y filters 54, 54'; and x filters 57, 57'. These filters are accurately matched, in order to provide the $\Delta V_x$, $\Delta V_y$ and $\Delta V_z$ signals. As with the position measurements, the clock signals from block 44 are connected through to each of the six filters, to provide digital filtering of the respective pairs of x, y and z signals. These six signals are amplified through amplifiers 51, 51'; 55, 55'; and 58, 58'; and then filtered through low pass filters 52, 52'; 56, 56'; and 59, 59'. The three pairs of x, y and z signals are then passed to computer 65 for carrying out the calculations set forth above, and determination of the a, b and c constants. Instead of using 2 sets of channel amplifiers and filters, only one set can be used, with each electrode alternatingly connected to the same channel input. Using the same channel for processing the signals ensures identical amplification, and thus greater accuracy.

Figure 3:
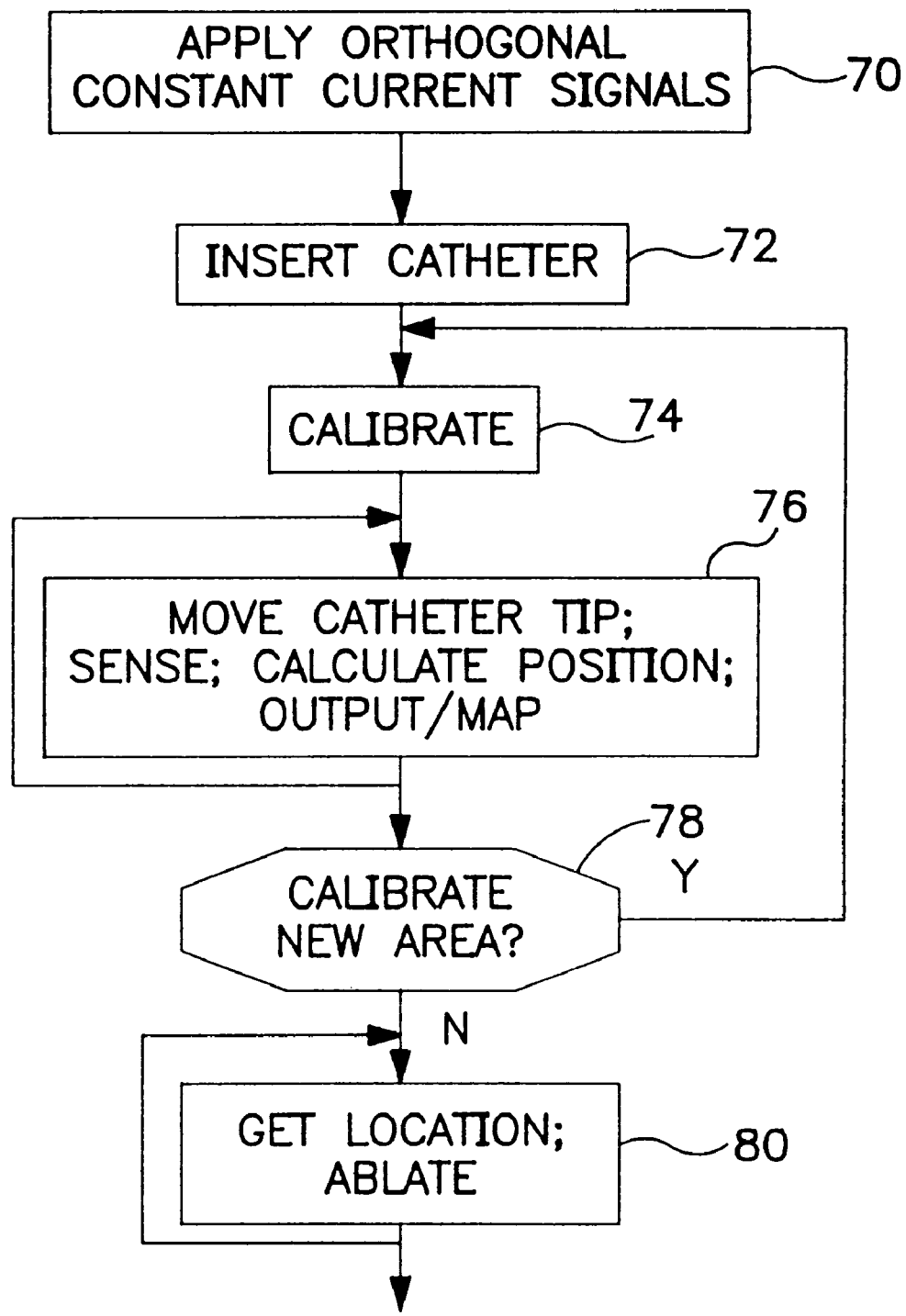
FIG. 3 is a flow diagram setting forth the primary steps of catheter mapping and ablation in accordance with this invention.

Referring now to FIG. 3, some of the salient steps taken in practicing this invention are set forth. At block 70, the orthogonal constant current signals are applied across the patient, as represented in FIG. 1. As indicated previously, these respective signals are suitably about 30, 31 and 32 kHz, each with a current of about 0.1 mA. While somewhat lower frequencies can be used, it is noted that lower frequencies, as well as higher currents, have the disadvantage that they are more likely to be picked up in ECG tracings. While higher frequencies are suitable and clearly within the scope of the invention, they require more exacting electronics. At 72, the step of inserting the catheter so that the tip is in the region to be mapped is indicated. This step may, of course, be performed before applying the orthogonal signals. At 74, the step of calibrating the system for determining the a, b and c constants is indicated. As set forth above, this step can be done simultaneously with taking location data. At 76, the catheter tip is moved into a position of interest. For a catheterization procedure which is to lead to ablation, sensing is performed to gather data relating to the heart, such as the location of an arrhythmia focus. Such data gathering techniques are well known in the art. The location information is determined, by the calculations set forth above, and the sensed information and location are stored and/or mapped. The flow diagram indicates that the steps of block 76 may be repeated any number of times, at the discretion of the physician. Thus, the catheter tip may be moved to any number of locations, all of which can be identified and automatically mapped in accordance with this procedure. Next, at block 78, it is determined whether there is a need or a reason to calibrate again, because of locating in a new area. As discussed above, it may be desirable to recalibrate if the catheter tip has been moved substantially, and, if so, the procedure goes back to 74. Again, note that the calibration can be undertaken together with the steps of moving the catheter tip, sensing, getting location, and mapping. When the mapping has been finished, the procedure goes to 80, for ablation. Here, the previously obtained mapping information is utilized to position the catheter tip, i.e., the catheter tip is moved and located, and when it is at the desired mapped position, ablation is performed for removing a source of the arrhythmia. As is known, ablation is suitably performed by applying a pulse of radio frequency energy to the heart tissue for a period of time, e.g., several minutes. The typical ablation procedure makes a lesion of about 1 cm in diameter. The ablation can be repeated at different locations in the vicinity of arrhythmia focus, using the previous mapping data, and determining the exact location, or position of the catheter tip in accordance with this invention.

Figure 4:
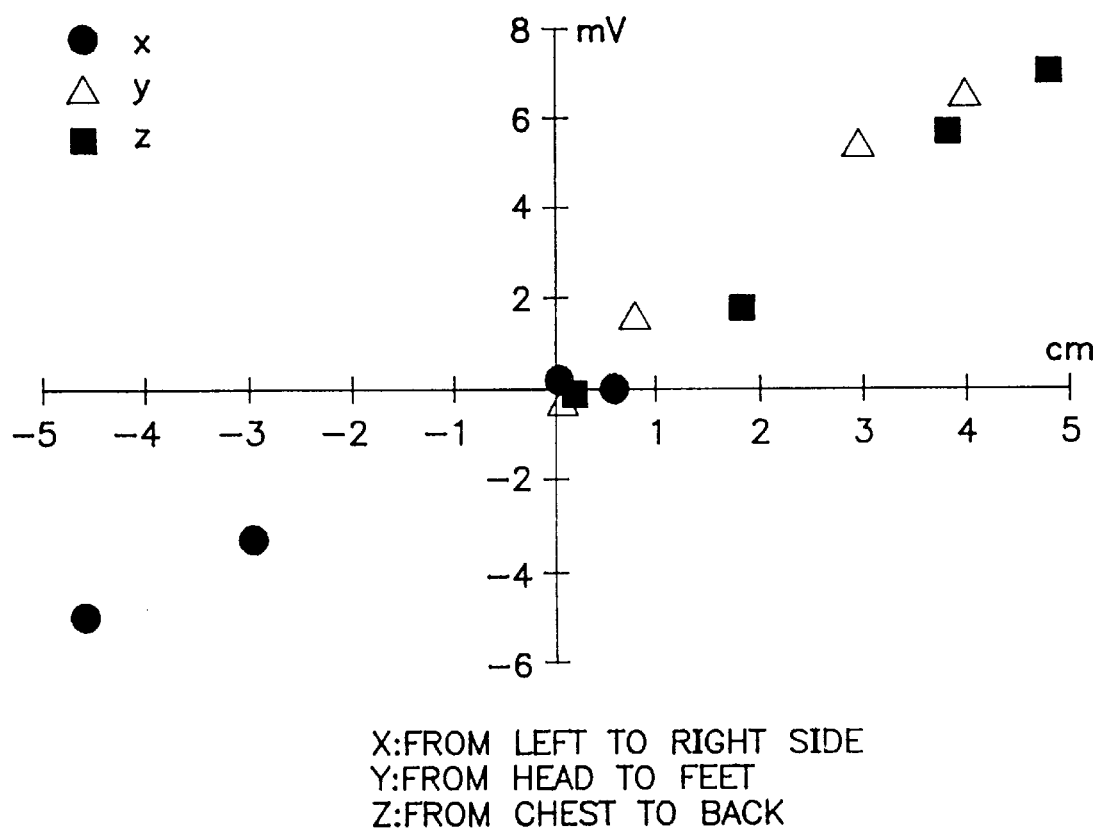
FIG. 4 is a diagram representing a plot of three-dimensional location data obtained in accordance with this invention.

Referring now to FIG. 4, there is shown an example of electrical localization, or position measurements, taken during a cardiac catheterization. A 10 kHz current at 0.1 mA pulse height, was delivered in three orthogonal directions through the patient chest. Referring to the legend of FIG. 4, X was left to right; Y was head to legs; and Z was frontal chest to dorsal. Actual catheter tip positions were measured by means of calibrated Roentgen images (centimeters, horizontal axis) and plotted versus measured electrical potentials amplified five times (mV, vertical axis), for each of the X, Y and Z directions. In this patient, the catheter tip was positioned at four different places, namely in the high right atrial appendage; on the bundle of HIS in the left ventricle near the mitral annulus; and inside the coronary sinus. One of the four positions is represented as the reference, at the intersection of the horizontal and vertical axes. Note that linearity for each of the x, y and z directions is very good. Heretofore, it has been very difficult to obtain a locational accuracy within several cm. With this invention, the accuracy is within mm, depending upon the degree of filtering of variations induced by respiration and heart movement. This accuracy leads to a significant improvement in ablation procedures, since previously after the initial mapping, the physician essentially had to again do fine tuning or remapping when returning to ablate. Using the technique of this invention, the physician can return very quickly to the primary ablation position, and reposition the ablation electrode for producing lesions at precisely defined positions so as to effectively cure and control the arrhythmia.

As discussed above, in the preferred embodiment, the reference electrode is placed somewhere on the skin, which has the advantage that it is unlikely to be displaced during the procedure. However, a disadvantage of this arrangement is that the cardiac contraction and respiration induced signal amplitude variations are relatively high. Another option is to use one electrode of a stable catheter within the body area, eg, heart, as the reference electrode. Positioning the reference electrode in another chamber of the heart has the, advantage that displacement is relatively unlikely; and respiration and contraction influences are reduced because for a given position of the mapping electrode, both electrodes move simultaneously with respiration and contraction. However, even here the reference catheter electrode may occasionally displace, which renders previous measurements substantially useless.

In another embodiment of the invention, and which addresses the need of a reliable reference electrode which has minimal sensitivity to contractions and respiration, the source electrodes are used also as reference electrodes, and the source signals are time multiplexed, as disclosed above. For example, a 90 kHz signal source is used, with respective successive pulses being connected across first the x–x' electrodes, next the y–y' electrodes, and then the z–z' electrodes, so that each pair of electrodes transmits a respective 30 kHz signal. In this case, separation of the sensed voltages is achieved by timing as contrasted to frequency, in a known manner. When one signal is being detected, the two other pairs of electrodes are available, and can be used as reference electrodes. For example, when either the x or y measurement is being made, both the z and z' electrodes are connected together as the reference electrode; when the z measurement is being made, the y and y' electrodes are connected as the reference electrode. The advantage of this arrangement is that the effective electrode is located roughly in the middle of the patient, close to the heart, and is not likely to dislocate because it involves skin electrodes.

It is to be noted that, with some of the source electrodes positioned around the heart, there may be some mapping locations which are rather close to a pair of skin electrodes. Due to the curvature of the equipotential lines of the resulting electric field, a slight error could be introduced when the mapping position is not roughly midway between the electrode pair. However, such an error can be compensated for by estimating the position of the mapping electrode between each such electrode pair, and making an appropriate mathematical adjustment. The approximate position of the mapping electrode can be checked by comparing the y voltage on the z–z' electrodes with the y voltageon the mapping electrode; comparing the z voltage on the y–y' electrodes with the z voltage on the mapping electrode; and comparing the x voltage on the y–y' and/or the z–z' electrodes with the x voltage on the mapping electrode.

The system and method of this invention are applicable to a number of important medical techniques. A primary application, as indicated above, involves identification of the focus, or exit-site of tachycardia, e.g., ventricular tachycardia (VT). As is known, in the catheterization process, surface ECGs are obtained during ventricular VT and compared with intracardiac ECGs obtained through the tip electrode at various places within the ventricle. By known techniques, the exit-site of the VT can be identified. By using the three-dimensional localization of this invention, the pacing sites and the corresponding correlations between paced and VT ECGs can be used to determine the optimal site at which the best correlation between both can be expected.

By way of further illustration of the scope of the invention, the system and method of this invention are also applicable for three-dimensional imaging of coronary stenosis. This can be done by combining echo tip data with three-dimensional data. A single catheter can be equipped with an echo tip at the end, as well as two distally located electrodes for obtaining dimensional information. By combining echo tip and three-dimensional data, an accurate three-dimensional map can be made for identifying coronary stenosis.

Yet another application is stent placement. By obtaining three-dimensional information in accordance with this invention, previously explored catheter positions can be accurately re-located so that a stent can be placed at exactly the same site where, for example, a PCTA had been applied, or where an intraluminal echo-image has been obtained. It is also to be noted that the technique can likewise be used for obtaining two-dimensional, or even one-dimensional position data, in applications not involving three-dimensional positioning.

While the invention has been illustrated by the use of orthogonal signals, they need not be absolutely orthogonal, although preferably substantially orthogonal. The angles may vary from strictly orthogonal and still be three-dimensional for purposes of practicing this invention; as long as the actual angles are known, a mathematical correction can be applied to compensate for any difference from truly orthogonal.

What is claimed is:

1. A system for determining the location of a catheter within a patient comprising
    means for applying at least two orthogonal current signals through the patient,
    a catheter adapted to be disposed within a patient, the catheter having means for sensing the applied at least two orthogonal current signals through the patient, and
    means for calculating from said sensed signal the location of the sensing means relative to the means for applying.

2. The system as described in claim 1 wherein each of the signals having a respective characteristic which renders it distinguishable from the other at least two orthogonal signals.

3. The system as described in claim 2 wherein the means for applying at least two orthogonal current signals comprises means for applying three-dimensional alternating orthogonal current signals.

4. The system as described in claim 3 said three-dimensional alternating orthogonal current signals corresponding substantially to x, y and z directions through said patient.

5. The system as described in claim 1 wherein the means for sensing the applied at least two orthogonal current signals comprise the catheter having a tip electrode.

6. The system as described in claim 1 wherein the means for sensing the applied at least two orthogonal current signals comprise a first electrode disposed on the catheter and a second electrode disposed on the catheter a predetermined distance apart from the first electrode.

7. The system as described in claim 6 wherein the second electrode is disposed on the catheter a predetermined distance longitudinally apart from the first electrode.

8. The system as described in claim 1 further comprising means for calibrating the correlation of the respective sensed signals with the catheter position.

9. The system as described in claim 8 wherein the means for calibrating the correlation of the respective sensed signals with the catheter position comprise a first electrode disposed on the catheter and a second electrode disposed on the catheter a predetermined distance apart from the first electrode.

10. The system as described in claim 9 wherein the second electrode is disposed on the catheter a predetermined distance longitudinally apart from the first electrode.

11. The system as described in claim 1 wherein the means for applying at least two orthogonal current signals through the patient comprises means for applying constant current pulse currents.

12. The system as described in claim 11 wherein the means for applying constant current pulse currents further comprise means for applying constant current pulse currents at frequencies in the range of about approximately 25–50 kHz, with the constant current pulses having a current in a range centered around about approximately 0.1 mA.

13. The system as described in claim 1 wherein said sensing means further comprise a narrow pass filter with the resulting signals passed through a low pass filter, the low pass filter having means for eliminating variations in the sensed signals due to cardiac contraction and patient respiration.

14. A system for use in indicating the location of a catheter within a patient, comprising:
    external signal means for applying at least one electrical alternating current signal to said patient;
    a catheter adapted to be inserted into said patient's body and manipulated to a plurality of locations, said catheter having at least an electrode; and
    location means connected to said electrode for sensing said at least one alternating current signal and processing said sensed alternating current signal to obtain location signals indicative of the location of said catheter when positioned at respective different body locations.

15. The system as described in claim 14 further comprising means for calculating from said location signals positions for each location where said alternating current signals were sensed; and output means for outputting data corresponding to said positions.

16. The system as described in claim 15, wherein said catheter comprises a pair of electrodes separated by a distance D, and comprising means for sensing calibration signals from said pair of electrodes, and calibration means for determining calibration factors from said calibration signals, said means for calculating comprising means for calculating said positions from said location signals and said calibration signals.

17. The system as described in claim 15, wherein said output means comprises video means for providing a three-dimensional representation of catheter location at each location to which it is manipulated.

18. The system as described in claim 16, wherein said reference electrode is a skin electrode.

19. The system as described in claim 14, wherein said location means comprises a reference electrode.

20. The system as described in claim 14, wherein said external means comprises means for applying three substantially orthogonal alternating current signals, three pairs of skin electrodes, and time means for time multiplexing said signals, and said reference electrode comprises selected pairs of said skin electrodes.

21. A method of locating the three-dimensional position of a catheter within a patient, comprising:
    applying respective three-dimensional orthogonal current alternating signals, corresponding substantially to x, y and z directions through said patient;
    inserting a catheter into said patient, said catheter having an electrode disposed along the catheter and sensing said applied respective three-dimensional orthogonal current alternating signals;
    measuring the signals sensed at said electrode and corresponding to each of said three dimensional orthogonal current signals;

calculating position data of the catheter from said sensed signals; and outputting position data representative of such three-dimensional position.

22. The method as described in claim 21 further comprising the step of obtaining correlation factors correlating the sensed measurements at said electrode with x, y and z positions within said patient.

23. The method as described in claim 22 further comprising the step of using said correlation factors to obtain the three-dimensional x, y and z position for each of said electrode positions.

24. The method as described in claim 22, comprising obtaining said correlation factors at positions where said position signals are also sensed.

25. The method as described in claim 22, comprising providing said catheter with two electrodes separated by a distance D, and wherein said obtaining step comprises obtaining sensed signals from said two electrodes corresponding to each of said x, y and z signals.

26. The method as described in claim 21, comprising generating said three dimensional orthogonal current alternating signals at respective different frequencies.

27. The method as described in claim 26, wherein said respective frequencies are in a range of about 25–50 kHz.

28. The method as described in claim 21, comprising time multiplexing said respective three dimensional orthogonal current alternating signals.

29. The method as described in claim 21, wherein said applying comprises applying constant current pulses, said pulses having a current of no more than about 0.1 mA.

30. The method as described in claim 21, comprising filtering said sensed signals to remove components attributable to cardiac contraction and patient respiration.

31. The method as described in claim 21, comprising using said outputted position data to map three dimensional position data.

32. The method as described in claim 21, comprising using a processing unit in real time to obtain said position data and visually displaying data representative of said obtained positions.

33. The method as described in claim 21, comprising manipulating said catheter to different positions within said patient's body, and outputting a visual representation showing the three dimensional location of each said different position.

34. The method as described in claim 21, comprising inserting said catheter into said patient's heart, and further comprising obtaining local activation data corresponding to each said obtained three-dimensional position, and storing said local activation data and said position data.

* * * * *